US006777699B1

(12) United States Patent
Miley et al.

(10) Patent No.: US 6,777,699 B1
(45) Date of Patent: Aug. 17, 2004

(54) METHODS, APPARATUS, AND SYSTEMS INVOLVING ION BEAM GENERATION

(76) Inventors: George H. Miley, 912 W. Armory Ave., Champaign, IL (US) 61821; Yasser R. Shaban, 17 El-Behira Street apt.803, Janaklees, Alexandria, ALX (EG)

( * ) Notice: Subject to any disclaimer, the term of this patent is extended or adjusted under 35 U.S.C. 154(b) by 0 days.

(21) Appl. No.: 10/396,668

(22) Filed: Mar. 25, 2003

Related U.S. Application Data

(60) Provisional application No. 60/367,696, filed on Mar. 25, 2002.

(51) Int. Cl.$^{7}$ .......................... A61N 5/00; G21G 5/00; G21K 5/10; H01J 37/08

(52) U.S. Cl. .............................. 250/492.3; 250/423 R; 250/492.2; 250/492.21; 250/492.22; 250/492.23

(58) Field of Search ............................ 250/398, 423 R, 250/492.2, 492.21, 492.22, 492.23, 492.3; 219/121.36, 121.52; 315/111.81

(56) References Cited

U.S. PATENT DOCUMENTS 4,783,595 A * 11/1988 Seidl ...................... 250/423 R
4,788,024 A 11/1988 Maglich et al.
5,457,298 A * 10/1995 Nelson et al. ......... 219/121.52
5,563,410 A 10/1996 Mullock
5,569,917 A 10/1996 Buttrill, Jr. et al.
5,578,831 A 11/1996 Hershcovitch
5,622,635 A 4/1997 Cuomo et al.
5,650,617 A 7/1997 Mordehai
6,107,628 A 8/2000 Smith et al.
6,188,066 B1 2/2001 Whitehouse et al.
6,291,940 B1 * 9/2001 Scholte Van Mast ... 315/111.81
6,392,187 B1 5/2002 Johnson
6,403,952 B2 6/2002 Whitehouse et al.
6,593,539 B1 * 7/2003 Miley et al. ........... 219/121.36

* cited by examiner

*Primary Examiner*—Nikita Wells
*Assistant Examiner*—Mary El-Shammaa
(74) *Attorney, Agent, or Firm*—Woodard, Emhardt, Moriarty, McNett & Henry LLP

(57) ABSTRACT

A high-perveance steady state deuterium ion gun was developed using a magnetic-index resonator in an Inductive Coupling Radio Frequency (ICRF) configuration. This approach made it feasible to generate an ion beam within millimeter dimensions extracted by negative potential placed at several centimeters from the exit of the ion source. The ion gun allows high extraction efficiency and low beam divergence as compared to other approaches.

20 Claims, 12 Drawing Sheets

METHODS, APPARATUS, AND SYSTEMS INVOLVING ION BEAM GENERATION

CROSS-REFERENCE TO RELATED APPLICATION

The present application claims the benefit of U.S. Provisional Application No. 60/367,696 filed Mar. 25, 2002, which is hereby incorporated by reference in its entirety.

BACKGROUND

The present invention relates to control and/or production of ion beams, and more particularly, but not exclusively, relates to ion beam gun designs and applications.

Ion beam source applications span a broad and immense spectrum of technologies. This spectrum includes solid state device fabrication, application of focused ion beams, surface modification, increased tool wear resistance, thin film deposition, semiconductor ion implantation, fabrication of molecular and macromolecular electronic devices, sheet metal processing, sputtering, scattering and backscattering studies, surface analytical techniques, fusion reactors, and ion-beam etching just to name a few.

Desirable goals for an ion source are a simple design, i.e. reasonable size relative to the applicant unit, and ease of maintenance. It is also desirable that the ion source should have "relatively" high extraction efficiency (current density/deposited power). It is often desired that the approach be scalable. Thus, there are many opportunities for further advancement in this area of technology.

SUMMARY

One embodiment of the present application includes a unique technique for generating ion beams. Other embodiments include unique methods, systems, and apparatus for ion beam generation and/or application, A further embodiment includes an ion beam gun comprised of an RF resonator, particle trap, and focusing arrangement. Optionally, this gun is coupled to a processing chamber to provide an ion beam thereto. The processing chamber can include a electrode positioned inside, and in one particular form inclues an inertial electrostatic containment device. One or more conveyor subsystems can be coupled to the processing chamber to deliver and/or retrieve work pieces.

In still a further embodiment, a system comprises a chamber coupled to a gas source, a resonator operable to ionize gas received in the chamber, a particle trap including several magnetic coils positioned about the chamber between the gas source and the resonator, and a focusing arrangement. In one form, the resonator includes an RF electrical energy source, a helical coil wound about a portion of the chamber and coupled to the RF electrical energy source, and an electrical shield positioned about the helical coil. Alternatively or additionally, the focusing arrangement may include an aperture device with an electrically floating portion and/or a magnetic focusing coil.

One object of the present application is to provide a unique technique for generating ion beams.

Another object of the present invention is to provide a unique method, system, or apparatus for ion beam generation and/or application.

Other objects, embodiments, forms, features, advantages, benefits, and aspects of the present invention will be apparent from the figures and detailed description provided herein.

DETAILED DESCRIPTION OF SELECTED EMBODIMENTS

Figure 1:
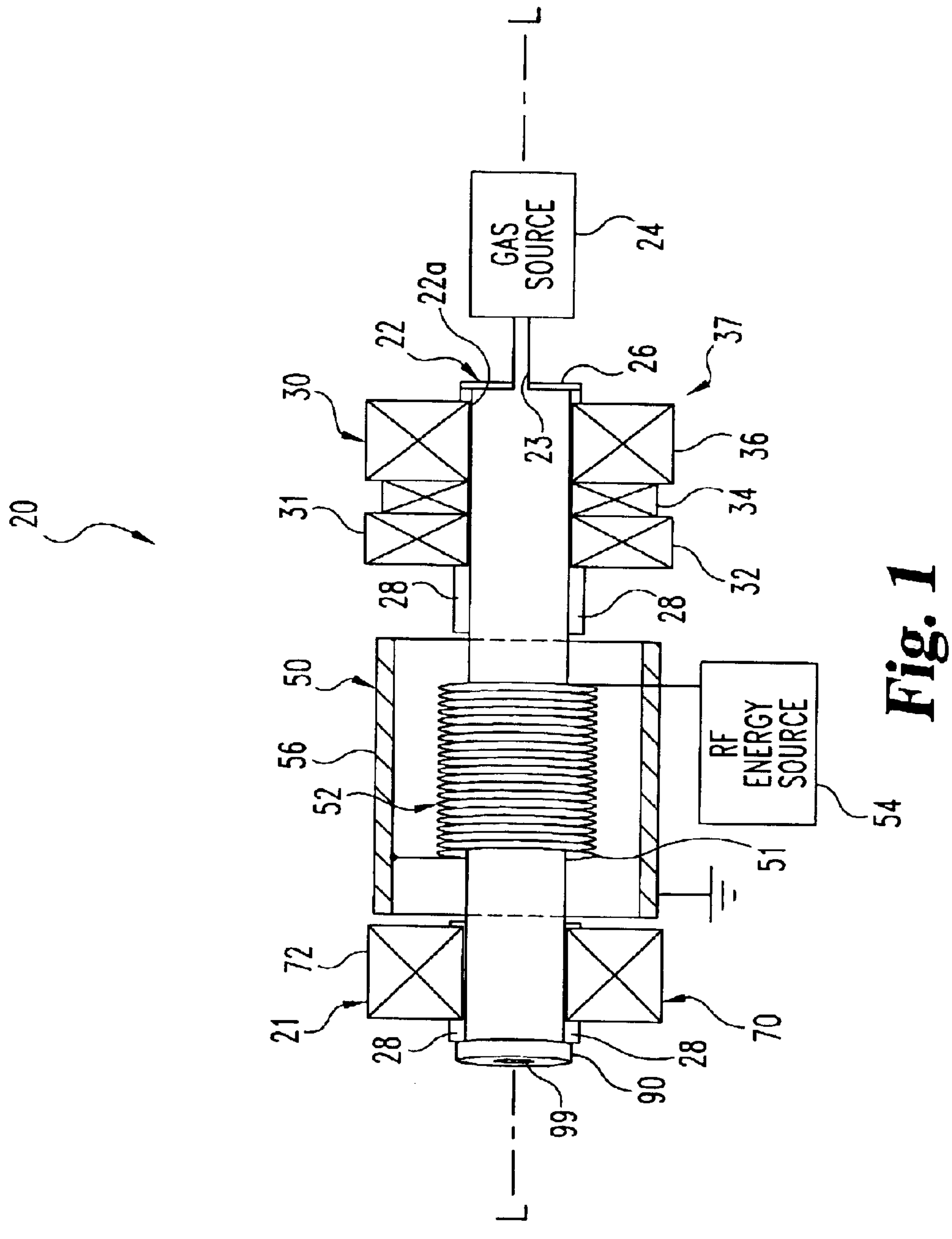
FIG. 1 is a partial sectional, diagrammatic view of an ion beam generation system.

For the purpose of promoting an understanding of the principles of the invention reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In one embodiment, the ion beam source device is constructed from an ionization source, a particle trap, and a particle focusing arrangement. The ionization source is constructed from two main parts: a helical antenna and a coaxial copper shield. In one example, FIG. 1 illustrates ion beam generation system 20 disposed along axis L and arranged to provide ion beam gun 21. System 20 includes ionization chamber 22 coupled to inlet 23 from gas source 24 by an electrically grounded flange 26. Chamber 22 is defined, at least in part, by tubular wall 22*a*. Wall 22*a* of chamber 22 is electrically grounded. System 20 also includes particle trap 30, resonator 50, and focusing arrangement 70 positioned along axis L and chamber 22 from right to left.

Gas enters chamber 22 through inlet 23 from source 24 and is ionized by resonator 50 to provide an ion source for beam generation. Resonator 50 includes helical coil 52 configured to operate as an RF antenna 51, Radio Frequency (RF) electrical energy source 54, and electrical shield 56 (shown in section). Coil 52 is wound about chamber 22, being approximately coaxial therewith. Coil 52 is positioned within shield 56 which is also approximately coaxial with chamber 22 and coil 52. Ionization results by applying a radio frequency (RF) electrical current from source 54 through coil 52 which radiates to ionize gas contained in chamber 22.

To ionize a gas with an RF antenna arrangement of this kind, one aspect of the radio frequency RF breakdown process is electron avalanche, which develops in the source gas when a strong enough electric field is applied to it. The avalanche is slowed down by electron energy losses and by the loss of electrons themselves. While the first losses slow down the ionization process (relative to atomic standard time). The later losses terminate chains in the multiplication chain reactions. When the production rate of electrons (avalanche) is balanced with the loss rate of electrons, the breakdown process approaches saturation. After reaching saturation, any excess power added to the discharge volume is generally wasted, with the conditions of the discharge kept constant. Gas breakdown is generally a threshold process so that breakdown starts only if the field exceeds a value characterizing a specific set of conditions. The relation between formation and removal of electrons determines the threshold of RF breakdown only if the field is maintained for a sufficiently long time—enough to produce numerous electron generations.

For Inductive Coupling Radio Frequency (ICRF), a high frequency "RF current" is passed through a solenoid coil that has several turns. The oscillating magnetic field of this current within the coil is directed along its axis and induces a vortex electric field. This electric field can ignite and sustain a discharge per relation (1) as follows:

$$\gamma[\exp(\alpha d)-1]=1 \quad (1)$$

Where $\alpha$ is Townsend's coefficient for ionization (# of ionization events performed by an electron per unit pass length along the field), $\gamma$ is effective secondary emission coefficient, and d is diameter of a tubular ionization chamber. The use of high frequency millimeter (mm) to ignite and sustain discharge plasma can have various advantages compared to the use of lower frequencies centimeter (cm) range. One advantage is that the induction electric field increases with increasing frequency in the absence of plasma. A typical frequency range of v is approximately 0.1–100 MHz. Another advantage is that the amount of energy reflected from the channel is very low because of the thin skin-layer effect.

In one form, coil 52 (antenna) was made from magnet wire of diameter $d_0$=1 mm wound in a single layer directly about chamber 22, which was in the form of a glass tube. For this form, coil 52 has about a 1 mm clearance from the surface of the tube and clearance between each coil turn is about 1 mm. An RF signal with a frequency of about 13.5 MHz was applied to the helical antenna, having N=43 turns. The antenna occupied an area of 10 cm×3.8 cm (length×diameter), and the length of the chamber tube was about 24 cm. The shield (13 cm length×10 cm diameter) was made from stainless steel with an inner copper coating of about 1 mm thickness. One end of the coil is attached to the shield (grounded) and the other end is attached to the RF generator, as is depicted in the embodiment illustrated in FIG. 1. This design was within ±10% of the design relations (2) through (8) provided as follows:

$$N = \frac{4826}{vD}\; N(\#\text{ of turns}),\ D \text{ in cm and } v \text{ in MHz} \quad (2)$$

$$0.45 < \frac{d}{D} < 0.6 \quad (3)$$

$$\frac{b}{D} > 1.0 \quad (4)$$

$$d_0 > 5\delta\; d_0 \text{ is wire diameter, and } \delta \text{ is the skin depth} \quad (5)$$

Figure 2:
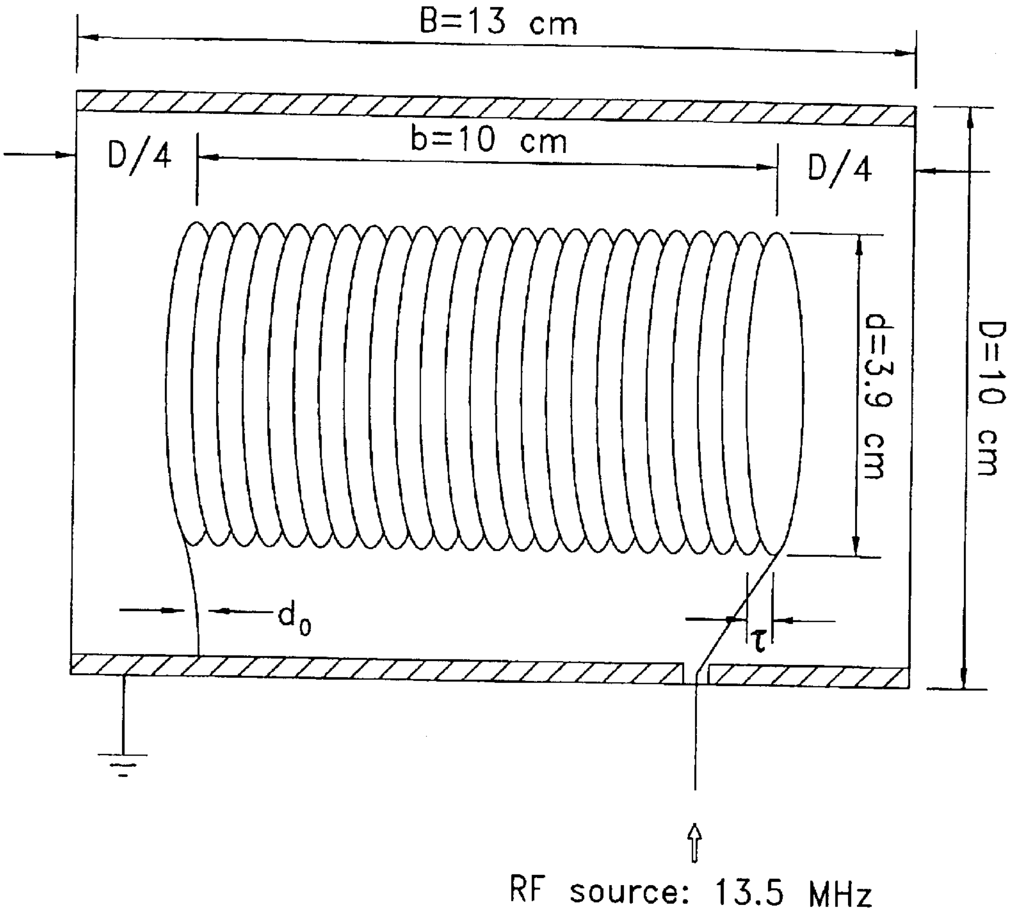
FIG. 2 is a partial, sectional, diagrammatic view of one form of an RF resonator for the system of FIG. 1.

-continued $$\delta(\text{cm}) = \frac{6.6\times10^{-3}}{\sqrt{v\,(\text{MHz})}} \quad (6)$$

$$0.4 < \frac{d_0}{\tau} < 0.6 \text{ at } \frac{b}{d} = 1.5 \quad (7)$$

$$0.5 < \frac{d_0}{\tau} < 0.7 \text{ at } \frac{b}{d} = 4.0 \quad (8)$$

where v is the applied frequency in MHz (MegaHerz) and the other symbols are indicated in FIG. 2, which shows certain details of this particular arrangement of coil 52. The clearance D/4 between the coil and the shield is desired to avoid voltage flashover. The coaxial copper shield cavity, 10 cm in diameter×12 cm length×0.1 mm thickness, has been found to enhance the coupling of RF electromagnetic waves into the chamber tube.

Referring back to FIG. 1, particle trap 30 is located between inlet 23 and resonator 50 along chamber 22. Particle trap 30 is in the form of an magnetic indexing arrangement 31 that includes several magnetic coils 32, 34, and 36 (collectively designated magnetic index coils 37). Magnetic index coils 37 are each wound about chamber 22 and are supported by rods 28 disposed along axis L and about chamber 22. In one form, rods 28 are comprised of stainless steel. Particle trap 30 operates by generating a differential magnetic field with magnetic index coils 37.

Figure 3:
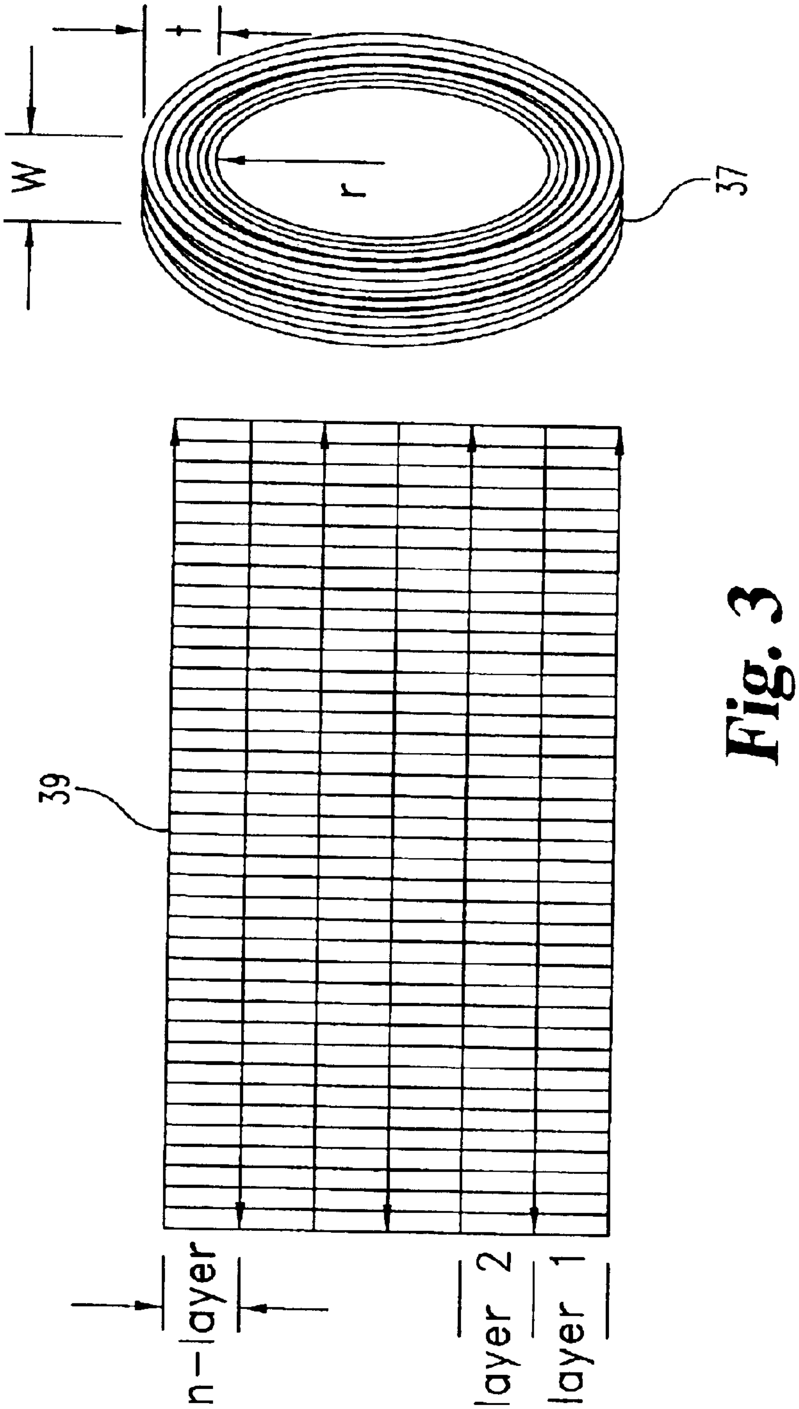
FIGS. 3 and 4 are partial diagrammatic views illustrating magnetic field coils for the particle trap of the system of FIG. 1.
Figure 4:
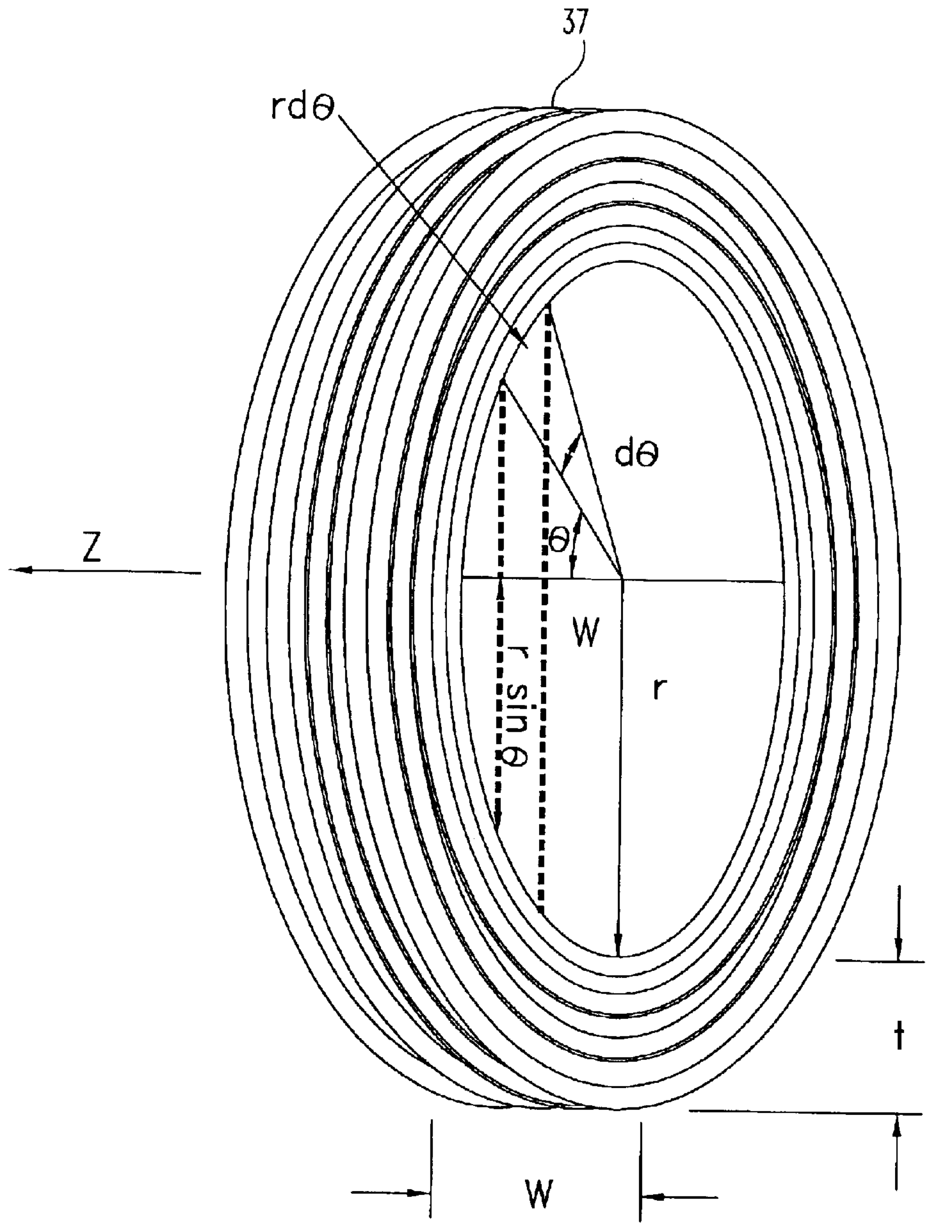

One example of coil 37 is illustrated in FIG. 3, in which the winding direction reverses from one layer to the next as represented by companion chart 39. As illustrated, the net radius of the coil is r+t which is greater than the width W. In one form, a magnet wire of ~2 mm diameter was wound in a configuration with reversing direction as shown by the arrows in chart 39. As a Direct Current (DC) is passed through coil 37 of several reversing turns (layers), an oscillating magnetic field results that is directed along an axis coincident with the origin of radius r and perpendicular to radius r. For coils 37 about chamber 22, this oscillating magnetic field results along axis L. Relation (9) gives the oscillating magnetic field, B, as follows:

$$B = \frac{\mu_0 \text{in}}{W} \quad (9)$$

where $\mu_0$ is the permeability of vacuum (equal to in SI units, $4\pi\times10^{-7}$ m.T/A), i is the DC current in amperes (A), n is the number of turns, and W is the coil length. Because the coil has a finite width W, the radius of the coil should be considered. In this case, we apply the Ampere's law according to FIG. 4, thus the oscillating magnetic field B in a finite solenoid is given by relations (10) and (11) as follows:

$$B\left[\int dw + R\int \cos\theta d\theta\right] = \mu_0 \text{ in} \quad (10)$$

Thus, $$B(W+R \sin 6)=\mu_0 \text{ in} \quad (11)$$

where the angular scaling degree $\theta$ is measured from the Z axis at the center point of the coil.

The condition for a long solenoid coil with a length approaching infinity is approximated as $\theta$=0. Where n is the total number of turns in Z and r directions, R is the net radius r+t, and $\theta$ is the angular scaling degree of the coil, measured at the center point of the coil in the Z-direction. As $\theta$ approaches zero, the second term of relation (11) vanishes. In contrast, the oscillating magnetic field in a solenoid of finite length is given by relation (12) as follows:

$$B = \frac{\mu_0 in}{W + R\sin\theta} \tag{12}$$

The radius of curvature $\Re$, Larmor radius, is given by relation (13) as follows:

$$\Re = 1.44 \times 10^{-4}\frac{M\sqrt{E}}{B} \tag{13}$$

where $\Re$, M, E, and B are in units of meters, atomic mass unit, electron volt, and Tesla respectively.

Figure 5:
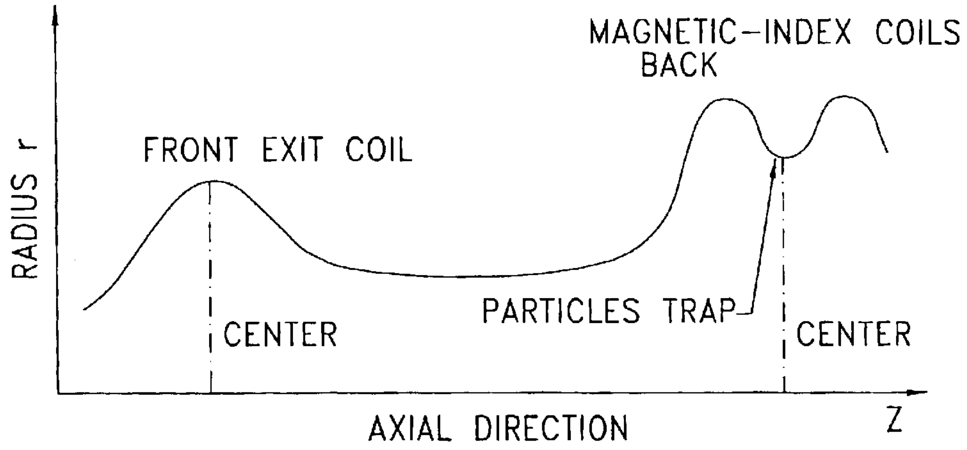
FIG. 5 is a graph illustrating certain operational aspects of FIG. 1.

The magnetic indexing arrangement 31 of trap 30 is configured to increase reflectivity of the ions generated by the RF field with resonator 50 through differential magnetic fields generated with coils 37. Accordingly, the loss of ions traveling from resonator 50 towards gas source 24 in chamber 22 is typically reduced. In the illustrated example, three coils 32, 34, 36 are electrically coupled in series from one to the next and powered by a DC electrical current source (not shown). The DC current was applied at constant rate in all coils 37. Coil 36, the farthest away from resonator 50, generates a magnetic field (B-field) greater than coil 34. Coil 34 operates as an anti-reflection field for coil 36, decreasing the reflectance. In an arrangement of coil 32 with a magnetic field (B-field) greater than coil 34 and approximately equal to coil 36, coil 32 operates as a reflector field to coil 34, and so on. The reflectivity of ions, i.e. the character of the particle trap increases with the number of magnetic-index coils as illustrated by the graph of FIG. 5. FIG. 5 shows a magnetic field distribution with a total magnetic field 0.075 Tesla (750 Gauss).

The ion beam source according to one embodiment of the present invention includes focusing arrangement 70 to focus ions as they exit through aperture 99. Arrangement 70 includes magnetic focusing coil 72 configured in a like manner to one of coils 37 previously described. DC current is applied to coil 72 at a constant rate to generate a corresponding magnetic field that varies with coil configuration, such as the number of coil turns and the coil width. Coil 72 is arranged to better focus ions by reducing the ion orbital radius and is also graphically represented in one empirical form by the "front exit coil" peak in FIG. 5. In one form these ions include deuterium molecular and atomic ions.

Figure 6:
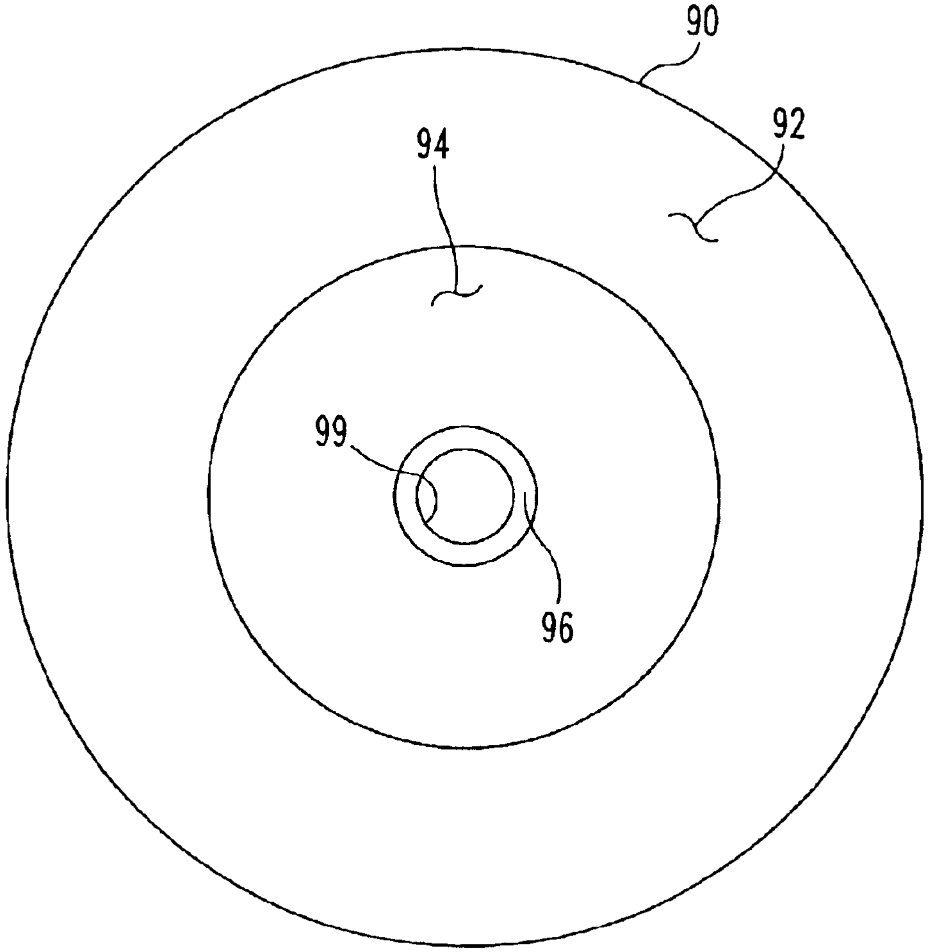
FIG. 6 is a front plan view of an aperture device of the system of FIG. 1.

Arrangement 70 also includes aperture device 90 defining aperture 99. A front view of device 90 is provided in FIG. 6. Device 90 is comprised of an electrically conductive outer ring 92 that is connected to chamber 22 and is generally at the same electric potential (ground for the illustrated chamber 22 of system 20). Concentric with ring 92 is an electrically insulating ring 94 connected to ring 92 and nested therein. Electrically conducting ring 96 is coupled to and nested within ring 94 and defines aperture 99 that is generally concentric with rings 92, 94, and 96. Because ring 94 electrically isolates rings 92 and 96 from one another, ring 96 and aperture 99 are electrically floating relative to the remainder of device 90 and gun 21. Accordingly, exiting ions are electrically isolated to reduce interference and/or deflection cause by the electric potential of chamber 22.

For various experiments described hereinafter, aperture device 90 (or floating nozzle) defines a central aperture of 1.5 cm in diameter and was made from three components: (1) a 2¾ inch flange (ring 92), (2) a 0.8 cm insulator layer made from Macor glass ceramic (ring 94), and (3) a stainless steel ring of 2 mm thickness (ring 96).

The ion beam gun 21 is operated such that the parameters: pressure, magnetic field, RF power, and the aspect ratio control its operation. Based on experiments, it has been found that for higher pressure operation greater than 1 mTorr, the magnetic field should be higher because the increase of pressure broadens the ion orbital radius. A wide range of deuterium gas pressures, 0.4 to 2 mTorr in the magnetic field range of 0.015 to 0.075 Tesla was utilized in experiments. An RF-based source of ionization was used to provide the ions for these experiments. The RF signal was first applied to an RF resonator (RF antenna) previously described to generate the ions. DC current was applied to magnetic indexing and focusing coils for these experiments at a generally constant level, with the coils being electrically coupled in series and operating at the same time. It was observed that the formation of a plasma column started to occur. The floating aperture device was made to electrically isolate the exit ions from the grounded wall of the chamber. The inner diameter of the aperture was about 1.5 centimeter (cm) in diameter. In still other embodiments, it is envisioned that RF power can be increased over 100 Watts with a differently arranged RF antenna and cooling system to handle anticipated heat.

Figure 7:
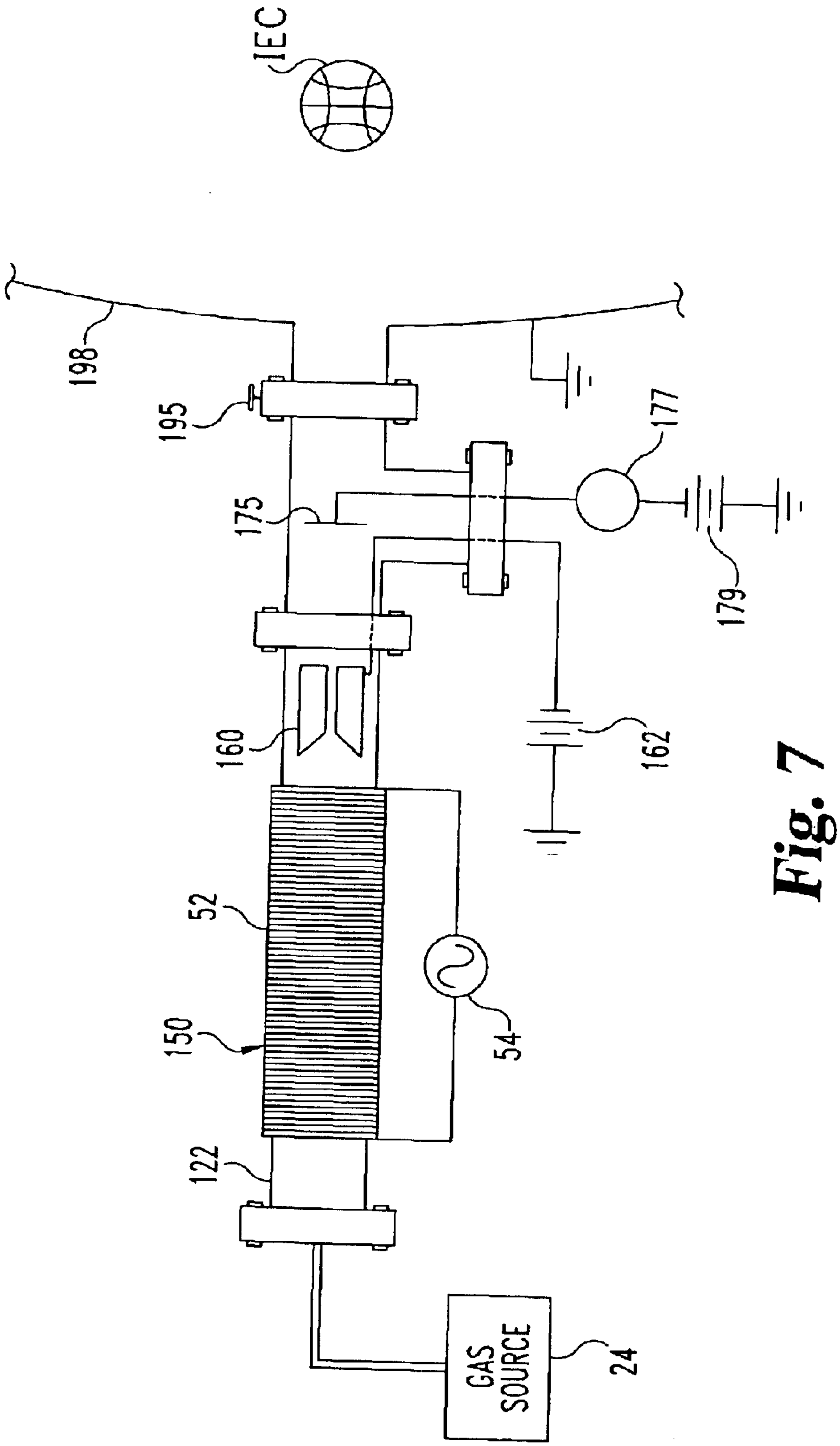
FIG. 7 is a partial diagrammatic view of an ion beam generation system coupled to a chamber enclosing an IEC.

A series of experiments were performed to develop suitable conditions for ion beam gun operation. A schematic representation of an ion beam gun according to the present invention with an ion extractor is shown as ion beam generation system 120 of FIG. 7. System 120 includes gas source 24 to supply gas to chamber 122 for ionization, resonator 150, extractor cone 160, and plate probe 175. Chamber 122 is tubular, generally has a cylindrical shape, and is electrically grounded. Resonator 150 includes helical RF coil 52 and RF electrical energy source 54 previously described. Extractor cone 160 is coupled to electrical energy source 162 to provide a desired electrical bias, and plate probe 175 is coupled to current meter 177 and electrical energy source 179 to provide a desired electrical bias. Chamber 122 is selectively coupled to Inertial Electrostatic Confinement (IEC) chamber 198 by valve 195. Chamber 198 contains an EEC device of a standard type.

Figure 8:
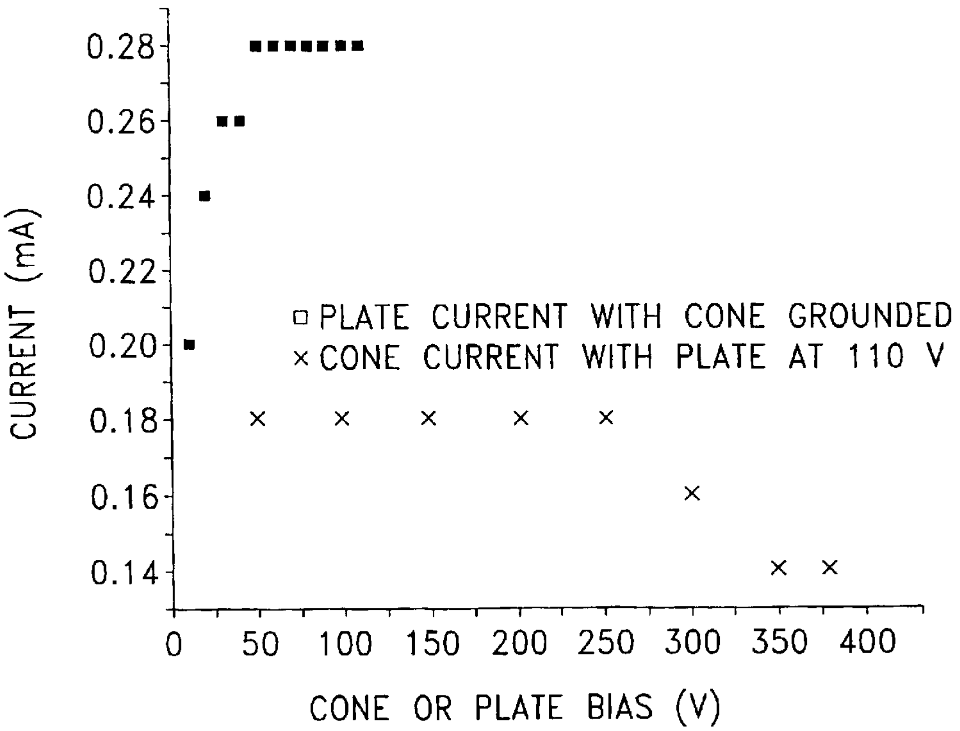
FIG. 8 is a graph illustrating certain experimental results obtained with the system of FIG. 7.

Extractor cone 160 is placed inside chamber 122 and biased negatively in some experiments and grounded in other experiments. A 2-cm disc plate probe 175 was placed at different positions from coil 52. The highest current was found to be 1.5 mA at 5 mTorr, at zero position from the edge of coil 52. The incident RF power was 250 Watts at 13.5 MHz, with average reflected power ~20%. At 7 cm away from coil 52, the current dropped to 0.3 mA at the same power level as measured with plate probe 175. For deuterium ion injection, extractor cone 160 was grounded and placed at a wall of the IEC chamber 198. The setup of IEC chamber 198 biases a target negatively at the center of the chamber with an electronically grounded wall i.e., the wall is electrically positive with respect to the center of IEC chamber 198. This kind of setup discriminates the electrons from the ion beam at the exit of the ion gun that is at the aperture of the gun. Several measurements were made with different extractor and plate conditions, and the results are shown in FIG. 8. The particle trap 30 and magnetic focusing coil 70 where not used in these experiments. It was found that ion beam collimation, observed for this form of the present invention, is not caused by IEC setup.

The aspect ratio, a/d, where a and d are the aperture radius and the extraction gap controls the amount of extractable current I given by the relation (14) as follows:

$$I \propto \sqrt{\frac{Z}{A}}\left(\frac{a}{d}\right)^2 V^{\frac{3}{2}} \qquad (14)$$

where Z, and A are the charge and mass number of ions respectively, and V is the extractable potential.

An ion beam source of the present invention can be constructed to vary with a number of parameters, such as pressure of the applied gas, the source of ionization, design of the magnet coils and their orientation, the size of the magnetic field, the aspect ratio, the floating aperture, and the location and size of the coaxial resonator. In certain experiments, an ion gun according to the present invention has been operated in different modes of pressure and magnetic fields. For example, a wide range of deuterium gas pressures, 0.4 to 2 mTorr was examined in the magnetic field range of 0.015 to 0.075 Tesla. Enlarging the activation area of the ion source caused a plasma column inside the ion source, and thus ions were accelerated by negative potential in a train fashion. The screening effect of the front ions on the back ones was not found to be significant for at least an arrangement where the aperture exit area is larger than the ion beam diameter (1.5 cm and 0.28 cm in certain experimental examples) because the negative potential field will penetrate inside the source and extract the back ions. Where the 0.28 cm beam diameter was measured 27 cm from the exit (likely being smaller at the exit).

Figure 9:
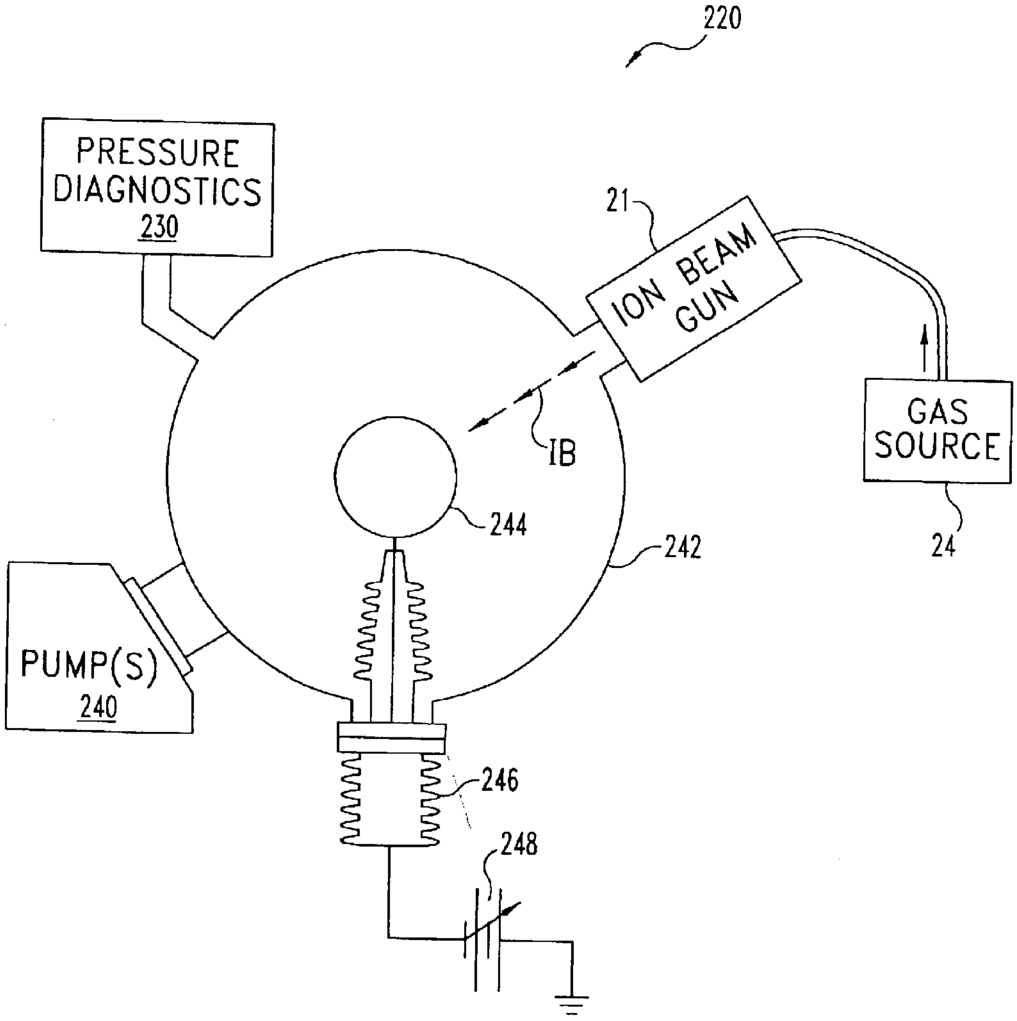
FIG. 9 is a partial diagrammatic view of an ion beam generation system for measuring ion current.

Several experiments were conducted with a spherical vacuum chamber to measure the maximum current deliverable from ion gun 21 using an experimental set-up like ion beam generation system 220 depicted in FIG. 9. System 9 includes ion beam gun 21 coupled to gas source 24 as previously described. Gun 21 selectively provides ion beam EB to the interior of spherical chamber 242 as represented by a series of arrows. The wall of chamber 242 is electrically grounded. Generally at the center of the interior of chamber 242 is an electrically conductive target 244 in the form of a stainless steel ball that is electrically insulated from the wall of chamber 242 by insulator device 246 and electrically biased by electrical energy source 248. Target 244 is biased negative relative to electrical ground and the wall of chamber 242. Pump(s) 240 to evacuate chamber 242 and pressure diagnostic equipment 230 are also operatively coupled to chamber 242.

With system 220, it was found that at low pressure and magnetic field, the maximum current was obtained. Measurements of beam currents were made at different pressures and at different magnetic fields. The pressure range was from 0.4 to 1.2 mTorr, with increments of 0.2 mTorr, with the exception that at 0.015 Tesla the pressure was raised to 2 mTorr. This was due to the fact that the ion power driven from gun 21 is very high and few readings would be obtained before an overload condition might be reached. The beam current measurements (1 mTorr and 2 mTorr) are shown in the graphs of FIGS. 10 and 11.

Figure 10:
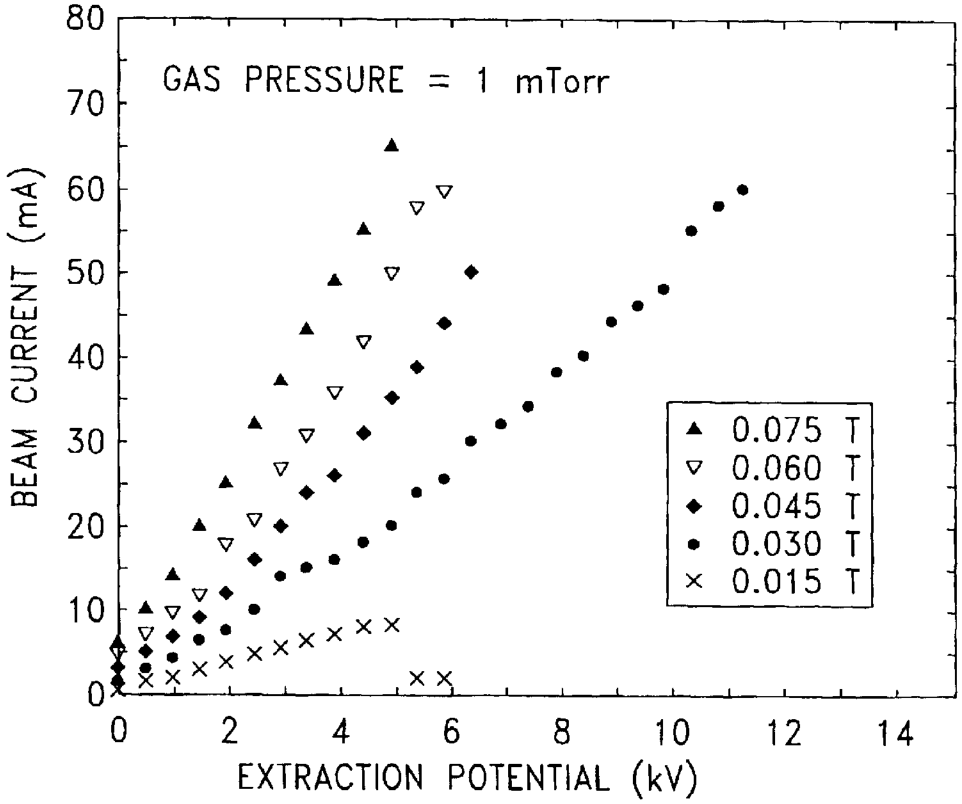
FIGS. 10 and 11 are graphs illustrating certain experimental results obtained with the system of FIG. 9.
Figure 11:
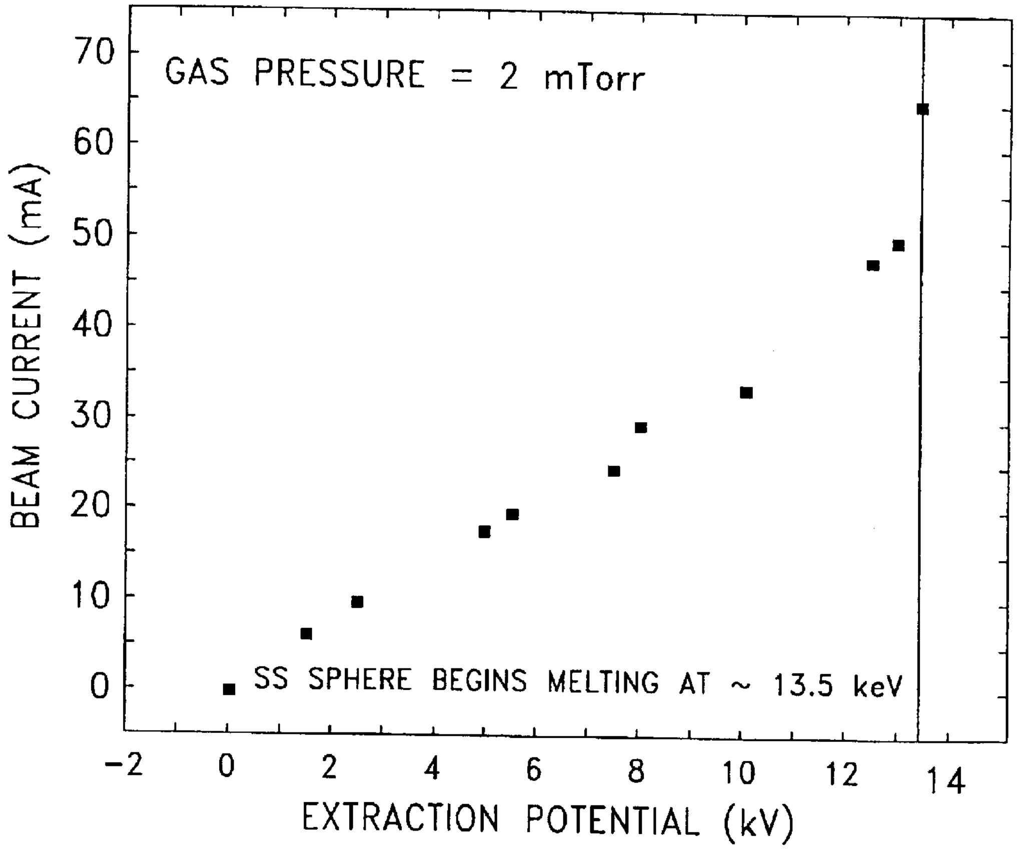

As shown in FIGS. 10 and 11, the ion current increases approximately linearly with the pressure at the same magnetic field. At 0.015 Tesla, the ion current increases slowly with increasing voltage to a peak value of 8.4 mA at an extracted voltage of 5 kV, and then it drops to 2 mA. As the voltage is tuned above 5 kV, the collected current remains constant at 2 mA. The slope of the ion current increases with the increase of the magnetic field and indicates that the peak current will be higher than that at a lower magnetic field. For a pressure below 1 mTorr, the peak current values were observed at a magnetic field greater than 0.03 Tesla.

To experimentally determine ion gun extraction efficiency, the center of chamber 242 was used as a target of the generated ion beam, with the wall of chamber 242 collecting electrons such that is acts as a discriminator. For these experiments, deuterium ions were used. For that purpose, a stainless steel ball of 101.6 mm diameter (0.5 mm thickness) was used for target 244 being placed in the center of chamber 242 (chamber diameter of about 55 cm). An electrical DC bias with a maximum of 100 kV and 50 mA was used for source 248. The ball is biased negatively and the wall chamber is grounded (positive with respect to the central potential). All experiments in the present setup, were performed below breakdown regime to avoid any contributions of background current to the one generated by the ion source. The breakdown potential was found to be ~50 kV at 2 mTorr and is greater at lower pressure, and this voltage is much larger than the extraction voltage applied to the ball for current measurements. The mean distance from the gun exit to the ball surface was 266.7 mm. The deuterium ion current measurements were performed with ion gun 21 in the pressure range of 0.4 to 2 mTorr. The total input power deposited in the gun (283.5 $cm^3$ tube volume) was varied according to the magnetic field as shown in Table I below while the RF power was fixed at 100 Watts:

TABLE I

| | | | | | |
|---|---|---|---|---|---|
| Total input power (Watt) | 121 | 184 | 289 | 436 | 625 |
| Magnetic field (Tesla) | 0.015 | 0.031 | 0.045 | 0.06 | 0.075 |

The ion beam efficiency is defined as how much current density is extracted per input power, or power density. The power density at different magnetic fields is listed in Table I for an active tube volume of 283.5 $cm^3$. At 0.4 mTorr and at 0.03 Tesla, the ion current increases slowly with he increase of the extracted voltage reaching a peak value of 11.5 mA at extracted voltage 5.5 kV and then drops sharply to 1 mA. As the voltage is tuned above 5.5 kV, the collected current remains constant at 1 mA. In a similar fashion, the peak and minimum currents measured at 0.045, 0.06, and 0.075 Tesla are as follows: 7.5, 0.8 mA; 15, 1.8 mA, and 25, 0.8 mA respectively. The peak current efficiencies are as follows: 6.5, 5.5, 1.0, and 1.6 $(A/cm^2)/(W/cm^3)$ for the magnetic fields 0.075, 0.06, 0.045, and 0.03 Tesla, respectively. The corresponding extraction energies are: 5,4.5, 3.5, and 5.5 keV respectively. The ion beam efficiency increases with the increase of the magnetic field except the results of 0.03 Tesla, which shows higher current values than the data at 0.045 Tesla. The differential ion energy distribution is very close to Gaussian. The energy spread value, ΔE½, corresponding to ½ΔIm (full width at half maximum) contains 76% of the total beam current. The energy spreads ΔE½, corresponding to 0.075, 0.06, 0.045, and 0.03 Tesla at 0.4 mTorr are: 2, 1.5, 1.0, and 2.5 keV, respectively. No data were obtained at magnetic fields greater than 0.075 Tesla. The ion beam efficiency increases with the increase of pressure at constant magnetic field in a linear relationship. It should be noted that the critical breakdown pressure with 100 Watt RF power was 0.4 mTorr. At 0.8 mTorr and 0.03 Tesla, the ion current increases slowly with the increase of the extracted voltage—reaching a peak value of 42 mA at extracted voltage 10 kV and then drops sharply to 3.4 mA. The peak ion beam efficiency is 3 $(A/cm^2)/(W/cm^3)$. The corresponding extraction potential and energy spread, ΔE½, are 10 keV and 4 keV respectively. As the pressure increases, the extraction potential and energy spread increase at constant magnetic field.

At 1.2 mTorr, no current peaks were obtained. It was observed, in the pressure range 0.4 to 1.2 mTorr, that the ion current is higher at higher pressure for constant magnetic field and extracted potential. For example the ion current at 0.03 Tesla and at 8 kV is 48 mA for 1.2 mTorr and 34 mA. At 0.045 Tesla and at 7 kV, the ion current is 55 mA for 1.2 mTorr and 48 mA for 0.8 mTorr. At 0.06 Tesla and at 6 kV, the ion current is 55 mA for 1.2 mTorr and 45 mA for 0.8 mTorr. At 0.075 Tesla and 5 kV, the ion current is 55 mA for 1.2 mTorr and 45 mA for 0.8 mTorr.

As the pressure increased from 1 mTorr to 2 mTorr, the extraction potential at the same magnetic field, for the same ion current, increased with pressure. FIG. 11 illustrates the ion current measurements at 2 mTorr. At this pressure, the ion beam melted an area of approximately 6.5 $mm^2$ in the stainless steel ball target at an extraction potential of 13.5 kV. The effective ion beam diameters were found to be inversely proportional to the applied magnetic field and increases with the increase of pressure. The increase of the ion current with the magnetic field is attributed to the reduction of the ion loss via the reduction of ions diffusing to the chamber wall. The introduction of a DC magnetic field changes the motion of the electrons' acceleration because the acceleration term changes as (e/m)(E+v×B), where B is the magnetic induction. When the magnetic field is applied along the cylindrical (for right circular finite cylinder) axis, the characteristic diffusion length $\Lambda_b$ can be replaced $\Lambda_b$ A, per relation (15) that follows:

$$\frac{1}{\Lambda_b^2} = \frac{1}{\Lambda_r^2}\left(\frac{v_m^2}{v_m^2+\omega_b^2}\right) + \frac{1}{\Lambda_z^2} \quad (15)$$

Where $\Lambda_r$ and $\Lambda_z$ are (R/2.405) and L/π respectively, and R is the radius of the tube. Thus the diffusion in a direction perpendicular to the magnetic field is reduced by an amount equivalent to increasing the dimension by a factor $$\left(\frac{1+\omega_b^2}{v_m^2}\right)^{1/2}$$

where $v_m$ is the electron collision frequency for momentum transfer, and is equal to $4.8\times10^9$ p ($H_2$), where p($H_2$) is in Torr and $v_m$ is in Hz, and $\omega_b$ is the electron cyclotron frequency and is equal to $$\left(\frac{qB}{m}\right).$$

If the mean free path between two collisions with gas atoms or molecules is on the same order or longer than the length of the ion orbital radius, then the analogy with light rays can be applied in the sense of using the properties: focusing, lineshape, pressure broadening, etc. The mean free path of atomic hydrogen varies from 2.2 mm at 0.4 mTorr to 0.44 mm at 2 mTorr as reflected in relation (16) that follows:

$$r = \frac{um}{qB} \quad (16)$$

Where u and m are the epithermal ion velocity and its mass, respectively. The epithermal ion velocity is given by relation (17) as follows:

$$u = 2\sqrt{\pi}\left(\frac{8kT}{\pi m}\right)^{1/2} \quad (17)$$

Substituting the appropriate numbers results in the ion radius of curvature varying from 12 mm at 0.015 Tesla to 2.4 mm at 0.075 Tesla. Additionally, the ion cyclotron frequency, u/r, varies from 0.52 MHz at 0.015 Tesla to 2.5 MHz at 0.075 Tesla. The width of the Lorentzian line shape, $\Delta V_h$, due to pressure broadening varies from 2.8 MHz at 0.4 mTorr to 14 MHz at 2 mTorr, here we used the epithermal ion velocity. Likewise, in a laser, if gas pressure is gradually increased in the laser cavity, the measured absorption profile of certain transitions in the gas atoms will change over from being Doppler-broadened at low pressures ($\Delta\omega_h<\Delta\omega_d$) to pressure broadened at high pressures ($\Delta\omega_h>\Delta\omega_d$). That is the width of the absorption (linewidth) profile gets wider as a result of the frequent atomic collisions due to the increase of pressure. As the pressure increases, the distance between molecules or atoms gets shorter and the collision events (field collisions) gets higher, and thus the generated ions follow the trends of the parent atoms. Therefore, at high pressure, when $$\frac{qB}{m}$$

$>\Delta v_h$, the ion radius of curvature is altered, and gets wider.

A microwave source is applied for the ion beam gun in another embodiment of the present invention. The use of high field frequency (~mm range) microwaves can result in a coupling power higher than the use of the long wavelength RF range due to the skin depth effect. The effective depth of penetration of a quasi-steady field into a conductor, δ, (skin depth) is given by relation (18) that follows:

$$\delta(\text{cm})=5.03/[\sigma f]^{0.5} \quad (18)$$

where σ and ƒ are the channel conductivity and field frequency in units of $(\text{ohm-cm})^{-1}$, and MHz respectively. In this case δ=0.11 mm for σ=60 $(\text{ohm-cm})^{-1}$ at mean temperature $10^4$ K for hydrogen plasma, and field frequency 3 GHz. The energy So deposited from the inductor into the conductor is inversely proportional to δ, $S_0\propto1/\delta$. For a thin skin layer, the coupling energy will be observed higher. In the microwave regime, a wave guide can be used as an active medium for ionization. This idea was illustrated by pumping a He—Ne laser (at wavelength 632.8 nm) within the guide itself. At about 10 GHz, rectangular, cylindrical, coaxial, and magic T wave guides all have typical dimensions of about 5 cm long and 3 cm in diameter or width. These configurations are usually coated with copper or made from copper. Copper has a skin layer in the microwave range on the order of 1 micron. The cylindrical guide is often desired because it generally has the highest quality factor (Q-value), which is about 11,600 (dimensionless) vs. 10,737 for a cube type, and 7,858 for a rectangular type. The Q-value is equal to the energy flowing in both directions through the guide of along a certain length divided by the energy dissipated per cycle in the walls and in the dielectric. The critical electron density given by relation (19) below as initiated by microwaves at a frequency of about 3 GHz is ~$10^{11}$ $cm^{-3}$, in this case the plasma frequency is 2.9 GHz. This frequency represents the cutoff point, (see relation (20) below) for which microwave power will be coupled into the plasma with minimum reflection. The cutoff point occurs when $n_e=n_{ec}$ or when $v_p=v$. For when $v_p>v$, waves generally cannot penetrate the plasma, undergoing significant reflection.

$$n_{ec}(cm^{-3})=1.24\times10^4 v^2, \qquad (19)$$

where v is the applied field frequency in MHz.

$$v_p(Hz)=(1/2\pi)5.65\times10^4\sqrt{n_e}, \qquad (20)$$

where $n_e$ is the electron density in $cm^{-3}$.

In another embodiment, an ion beam gun according to the present application is to provides a steady state neutron source; ~$10^{11}$ n/sec for IEC applications. A wide range of deuterium pressure from 0.4 to 2 mTorr was examined in the IEC below breakdown region, and high current extraction efficiency and flux were obtained in this range. A neutron rate of $2\times10^7$ n/sec was achieved at 75 kV, 15 mA, and 1.2 mTorr deuterium pressure in the IEC with the gun at 100 Watt RF power and at 0.06 Tesla. The maximum current measured from the ion gun at 1.2 mTorr is expected to be greater than or equal to 150 mA (the measured non-saturated value was 75 mA), corresponding to ion flux of $5.7\times10^{18}$ ions/($cm^2$-sec). Assuming a linear relationship between neutron rate and beam current, the neutron rates of $2\times10^8$, at 100 Watt of RF power at 0.06 Tesla, and $2\times10^9$, at 1 kW RF power at 0.06 Tesla would be achievable from DD nuclear reactions at the same extraction efficiency.

The neutron production efficiency (n/J) of the present results and other EEC setup is compared as shown Table II. It has been discovered from operation of the ion gun that a "ion-gun driven discharge" mode was obtained. This happens when the chamber pressure is too low to allow a discharge at the cathode potential, but once ions are injected into the vessel from the ion gun, a discharge follows with the major microchannels forming along the axis of the gun. Once the gun is turned off, this driven discharge is extinguished. The electron emitting coils were effective in achieving a slight reduction in background pressure. The emitter experiments were in general successful in producing added ionization, but at the expense of considerable added input power. Since the primary objective of IEC fusion research is to achieve an increased Q value (electrical power in/fusion power out), efficiency is a major parameter in deciding which ion source to use.

TABLE II

| Type of technique | Neutron/Joule | Pressure (mTorr) | IEC volume $m^3$ |
|---|---|---|---|
| IEC + ILLIBS | 12,040 | 1.2 | 0.092 |
| IEC, pulse mode | 1,460 | 7.5 | 0.092 |
| IEC+ filament | 6,680 | 2.0 | 0.422 |

For the current measurements the maximum extractable voltage, corresponding to peak current 150 mA, will be ~15 kV at 0.06 Tesla and at 1.2 mTorr. To obtain the same peak current but at 75 kV, one has to lower the aspect ratio of the ion gun; a/D where a is the aperture radius and D is the extraction gap between the gun exit and the maximum potential point. The aspect ratio is, for the present case, equal to 0.028. Because the extractable potential $V\sim(D/a)^{1.3}$, thus increasing the distance or reducing the aperture radius will shift the data toward higher voltage. The reduction on the aperture radius (with constant magnetic field) is generally not desirable, here, since a portion of the deuterium ions, particularly, at high input power where the beam diameter is expected to be bigger than at 100 Watt will be blocked by the exit aperture (nozzle). On the other hand an increase of the extraction gap by a factor of 3.5 will shift the maximum voltage from 15 to 75 kV. The aspect ratio for high neutron yield will be 0.008, and this can be made by reducing the size of the grid or by increasing the vessel diameter or by adding some flanges between the gun exit or a combination of all previous variables. To obtain $2\times10^9$ n/sec, at 1.2 mTorr and at 0.06, a 1.5 A current is utilized with 1 kW RF power. The beam diameter was measured at the above condition to be 1.5 mm, and the aperture (nozzle) diameter is 15 mm. In this case, the beam diameter will be an order of magnitude higher, i.e. 15 mm, and this is equal to the aperture diameter. The aspect ratio remains the same as before.

As an alternative or addition to EEC and/or neutron source applications, such as DD nuclear reactions, ion beam applications span a broad and immense spectrum of technologies. This spectrum includes applications in the fields of solid state device fabrication, focused ion beams, surface modification, increased tool wear resistance, thin film deposition, semiconductor ion implantation, fabrication of molecular and macromolecular electronic devices, sheet metal processing, sputtering, scattering and backscattering studies, surface analytical techniques, fusion reactors, and ion-beam etching just to name a few. Typically, ion-beam sources have fluxes ranging from $10^{-3}$ to $10^{16}$ ions/$cm^2$/sec. Ion flux has been found to be desirable in determining which mechanisms dominate in the sputtering of potential PFC materials.

Indeed, sputtering is used widely. Thin films of refractory metals, like W, Mo, and Ta, are made by ion sputtering or by electron-beam technology. Reactive sputtering is used to make oxide, nitride, sulfide, and carbide films by adding $N_2$, $O_2$, $H_2S$, and $CH_4$, respectively to argon. Sputtering is also used to apply antireflection coating to optical glass and to coat isolators. Sputtering equipment can use both gas discharge and ion beams. Ion beams have a greater ease of control over energy, current, and beam divergence when compared to plasma sputtering. Further, the possibility of lowering the pressure into the range of 1–100 mPa (0.75 mTorr=0.1 Pa) (two orders of magnitude less than that with standard plasma processing) is frequently desirable so that the mean free path of primary ions and sputtered atoms exceeds the chamber dimension. Ion beams allow direct film deposition with generally better adhesion and uniformity compared to other schemes. Also, Ion-Beam-Assisted deposition can be used in the production of thin dielectric films for which certain optical properties are often desired. The ion beam sources of the present application provide a much more cost effective beam than conventional arrangements.

In another application, precise doping of Si and GaAs is often desired in certain semiconductor operations. For such applications, a high-energy ion loses energy in elastic and inelastic collisions until it comes to rest in a crystal lattice. Penetration depth depends on its energy, mass, and charge state as well as on the substrate material. Energies of 10–100 keV produce penetration of ~10–20 nm.

The ion gun embodiments of the present invention are also desirable for plasma processing applications, e.g. serving as an intense source for metallic plasma production. Ion sources are currently used to melt refractory metals, like W, Mo, Ti, Ni, Zr, and alloys thereof to produce special steel. They also are used in select steps for metallic plasma production which processing plays various roles in metallurgy and chemistry. Examples include reduction of iron from ore or recycling scrap iron, production of aluminum and different alloys, recycling of platinum from car catalysts, and re-melting under low pressure to improve metal properties. One advantage of a plasma-based plant for iron oxide reduction as compared to conventional blast furnaces is a higher efficiency. In a related field, certain plasma chemistry processes can be used for treatment of hazardous chemical waste (e.g. dioxin).

Figure 12:
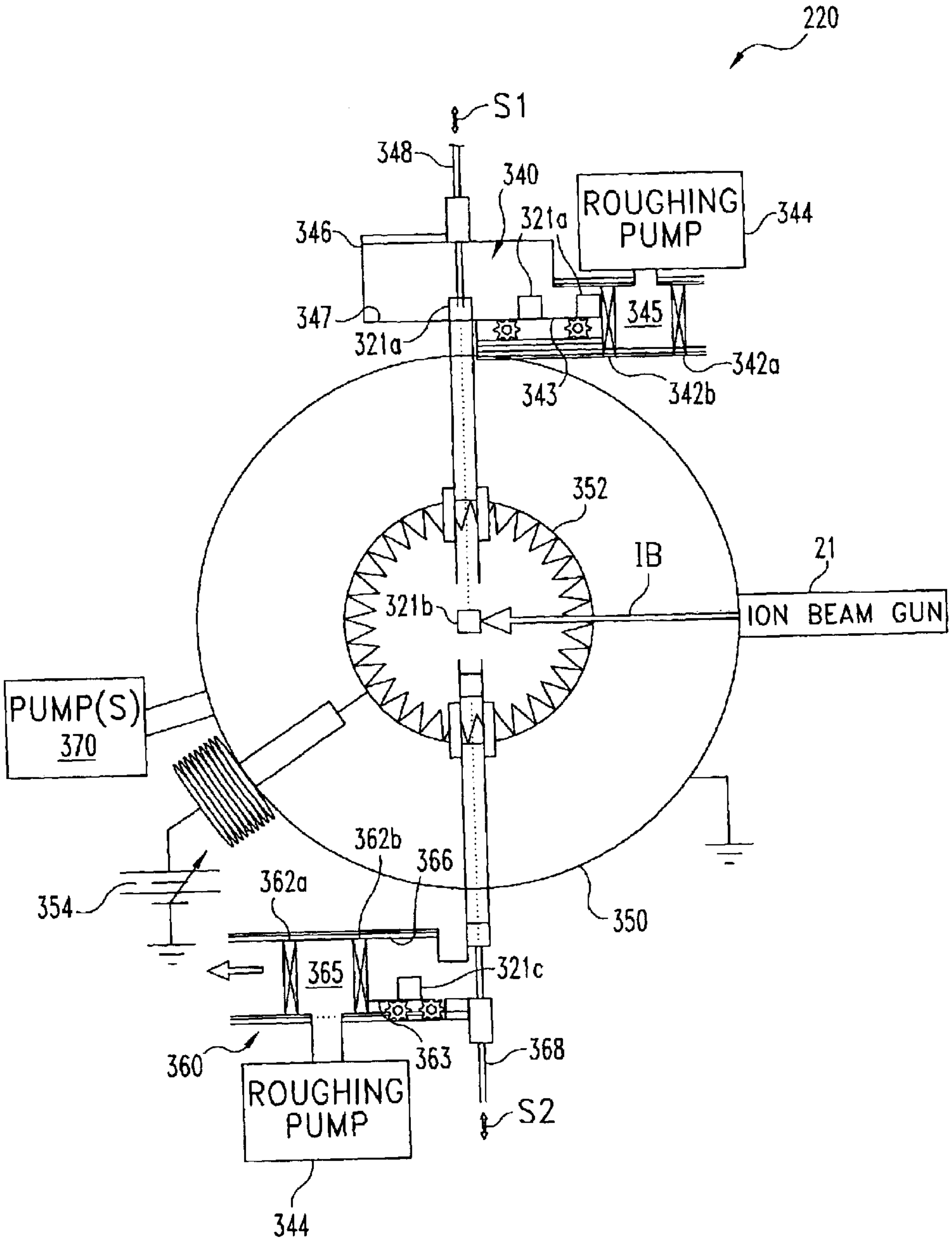
FIG. 12 is a partial diagrammatic view of a system for processing a work piece with a single mode of operation.

Referring to FIG. 12, ion beam processing system 320 is illustrated. System 320 includes ion beam gun 21 as previously described, upper conveyer subsystem 340, processing chamber 350, and lower conveyor subsystem 360. System 320 is arranged for operation in a single-mode industrial application by accepting unprocessed work pieces 321*a* one at a time from upper conveyor subsystem 340, processing each work piece 321*b* in chamber 350 with ion beam IB, and receiving each processed work piece 321*c* with lower conveyor subsystem 360. Chamber 350 is of the spherical type previously described with an electrode 352 generally centered therein. The chamber wall is electrically coupled to ground and is electrically positive relative to electrode 352, such that electrode 352 operates as a cathode. Variable electrical energy source 354 maintains the electrical bias of electrode 352 relative to electrical ground (and chamber 350).

Upper conveyor subsystem 340 includes two gating valves 342*a* and 342*b*, work piece carrier 343, moderate pressure compartment 345, vacuum compartment 346, and upper conveying shaft 348. Valve 342*a* is exposed to air and is opened when work pieces 321*a* are inserted for processing, then it is closed. Work pieces 321*a* are placed in compartment 345 for moderating the pressure to the mTorr range with roughing pump 344 while both valves 342*a* and 342*b* remain closed. Valve 342*b* is opened after pressure inside compartment 345 reaches this range. Work pieces 321*a* are placed on carrier 343 and delivered to vacuum compartment 346 as maintained by pump 347. Valve 342*a* remains closed during this transfer to avoid air contamination. Once in compartment 346, conveying shaft 348 captures a single work,piece 321*a*. Shaft 348 selectively moves (translates) in the directions indicated by double-headed arrow S1 to move the captured work piece 321*a* into chamber 350, approximately centering it within grid 352; and then returns to compartment 346 to capture the next work piece 321*a*.

Once placed in chamber 350, work piece 321*b* is exposed to an ion beam IB generated with gun 21, as indicated by the arrow in chamber 350. This exposure may include, but is not limited to sputtering, ion implantation, or metallurgical treatment, to name only a few. After processing, shaft 368 of lower conveyor subsystem 360 captures each processed work piece 321*b*, controllably moving in the directions indicated by double-headed arrow S2. Subsystem 360 includes lower vacuum compartment 366 that accepts each processed work piece 321*c* from shaft 368. Vacuum pump(s) 370 are coupled to chamber 350 to maintain a desired vacuum level therein.

Subsystem 360 also includes carrier 363, two gating valves 362*a* and 362*b*, and compartment 365. Each processed work piece 321*c* is placed on carrier 363 and moved to compartment 365 while valve 362*b* is held open and valve 362*a* is closed. Valve 362*a* is opened to permit each processed work piece 321*c* to exit subsystem 360 after closure of valve 362*a* to avoid air contamination inside the main chamber. Compartment 365 is selectively evacuated to the mTorr range with roughing pump 344.

Figure 13:
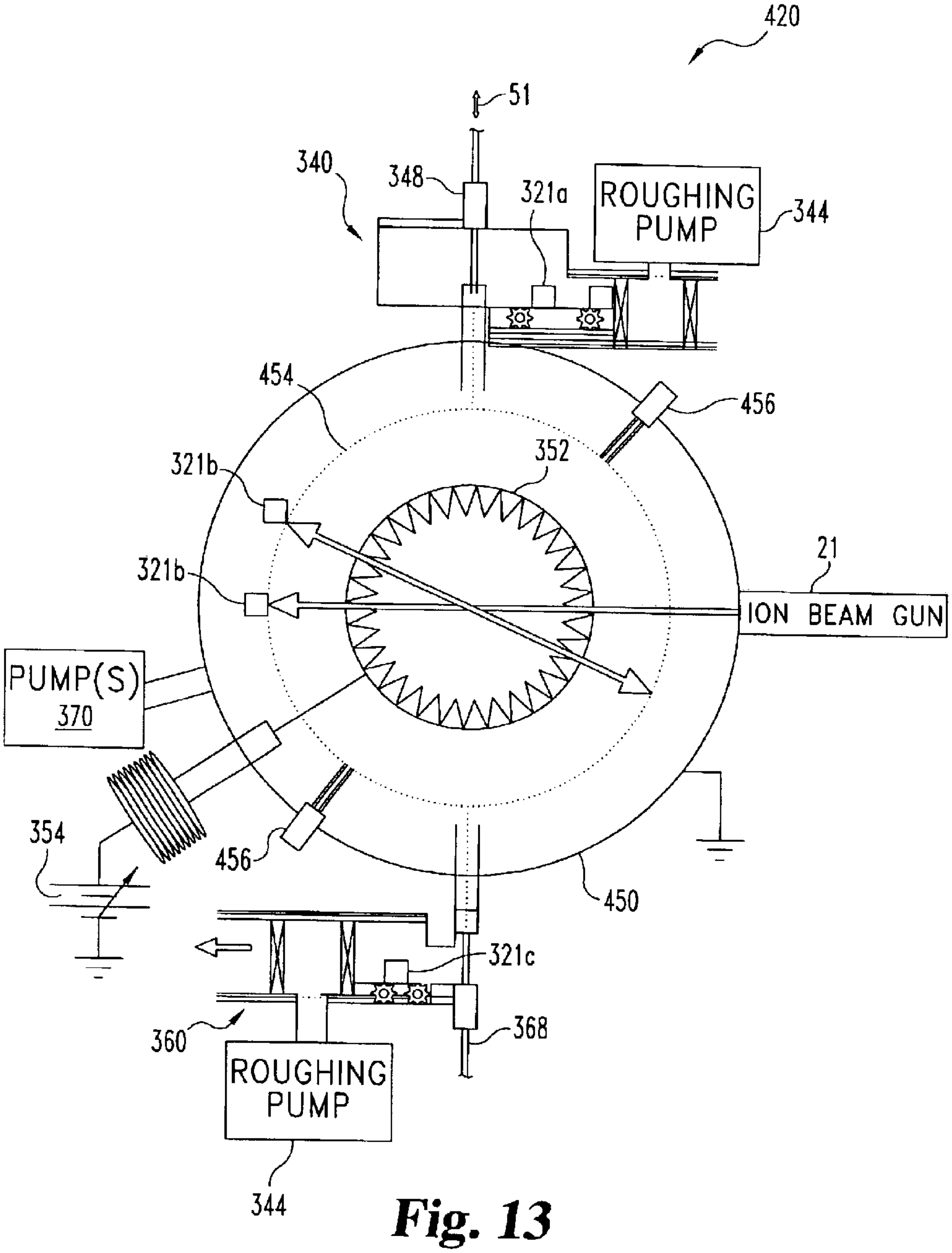
FIG. 13 is a partial diagrammatic view of a system for processing a work piece with multiple modes of operation.

Referring to FIG. 13, ion beam gun processing system 420 is illustrated where like reference numerals refer to like features. System 420 includes spherical chamber 450 coupled to upper conveyor subsystem 340 and lower conveyor subsystem 360 previously described. Chamber 450 is of the type previously described with electrode 352 generally centered therein. The chamber wall is electrically coupled to ground and is electrically positive relative to electrode 352, such that electrode 352 operates as a cathode. Variable electrical energy source 354 raintains the electrical bias of electrode 352 relative to electrical ground.

System 420 conveys work pieces 321*a* from upper conveyor subsystem 340 to chamber 450 and also conveys processed work pieces 321*c* from chamber 450 to lower conveyor subsystem 360 in the same way as described for system 320. In contrast, chamber 450 is configured for multimode processing. Inside chamber 450 about cathode 352 is conveying ring structure 454 supported by insulated supports 456 and controlled by a DC motor (not shown) located outside chamber 450. Instead of inserting the work piece 321*b* inside electrode 352, each work piece 321*b* is carried by ring structure 454 about electrode 352 A multi-directional ion beam tracing inside the electrode 352 is illustrated in FIG. 13.

There are many other embodiments of the present invention envisioned. One embodiment includes a unique coaxial resonator. In one form, this resonator includes a helical RF antenna in the form of a coil wound about a chamber defining wall. The chamber is configured to receive a material from which ions are to be generated. The helical antenna and chamber wall are surrounded by an electrical shield. The ion source material could be deuterium or another type of gas, evaporated from a liquid and/or originating from a solid.

In another embodiment, a charged particle trap is formed by a series of coils from which the direction of winding reverses. The coils of the trap vary in geometry to provide a differential magnetic field to trap, redirect, and/or reflect desired particles. In a further form, the coils are positioned relative to a chamber to receive ions from an ion generation source. By way of nonlimiting example, this source could include an RF antenna, such as the above-described coaxial resonator. In one implementation of this form, one of the coils nearer to the antenna generates a magnetic field greater than a second one of the coils, and a third one of the coils generates a magnetic field greater than the second one of the coils. In still other forms, differential electrostatic techniques are utilized to trap charged particles as an alternative or addition to magnetic differential fields provided by a number of coils.

A further embodiment includes a particle focusing device in the form of a magnetic or electrostatic lens and an electrically floating aperture device configured to receive a stream of charged particles for output. In one form, these devices are positioned downstream of an ion generating source and/or a particle trap. In one variation of this form the ion generating source includes a resonator with an RF coil antenna within an electrical shield and the particle trap is comprised of a number of coils of different geometry for which the direction of winding reverses from one layer to the next.

All publications, patents, and patent applications cited in this specification are herein incorporated by reference as if each individual publication, patent, or patent application were specifically and individually indicated to be incorporated by reference and set forth in its entirety herein. While the invention has been illustrated and described in detail in the drawings and foregoing description, the same is to be considered as illustrative and not restrictive in character, it being understood that only the preferred embodiments have been shown and described and that all changes, modifications and equivalents that come within the spirit of the invention as defined by the following claims are desired to be protected. In reading the claims it is intended that when words such as “a”, “an”, “at least one”, and “at least a portion” are used there is no intention to limit the claims to only one item unless specifically stated to the contrary in the claims. Further, when the language "at least a portion" and/or "a portion" is used, the claims may include a portion and/or the entire items unless specifically stated to the contrary.

What is claimed is:

1. An apparatus, comprising:

a chamber coupled to a gas source;

a resonator operable to ionize gas received in the chamber from the gas source, the resonator including an RF electrical energy source, a helical coil wound about the chamber and coupled to the RF electrical energy source and an electrical shield positioned about the helical coil;

a magnetic indexing arrangement including several magnetic coils positioned about the chamber between the gas source and the resonator to control ion movement; and a focusing arrangement including an aperture device, the aperture device including a portion that is electrically floating relative to a wall of the chamber coupled to the aperture device.

2. The apparatus of claim 1, wherein the focusing arrangement includes a magnetic focusing coil positioned between the resonator and the aperture device.

3. The apparatus of claim 1, further comprising a processing chamber coupled to the chamber to receive an ion beam from the aperture of the aperture device.

4. The apparatus of claim 3, further comprising an electrode positioned in the processing chamber and electrically isolated therefrom.

5. The apparatus of claim 4, further comprising a first conveyor subsystem coupled to the processing chamber to deliver work pieces to the processing chamber.

6. The apparatus of claim 5, further comprising a second conveyor subsystem coupled to the processing chamber to retrieve work pieces from the processing chamber.

7. The apparatus of claim 4, wherein the processing chamber is electrically grounded and the electrode is negatively biased relative to electrical ground.

8. The apparatus of claim 3, further comprising an inertial electrostatic containment device positioned in the processing chamber.

9. The apparatus of claim 1, wherein a first one of the magnetic coils is configured to generate a magnetic field strength greater than a second one of the magnetic coils.

10. The apparatus of claim 1, wherein the magnetic coils each include a winding that reverses direction.

11. A system, comprising: an ion beam gun, the ion beam gun including:

a chamber coupled to a gas source;

means for ionizing gas received from the gas source, the ionizing means including a helical coil and an electrical shield positioned about the helical coil;

means for controlling movement of ions generated with the ionizing means; and means for focusing ions received from the ionizing means, the focusing means including a magnetic coil and an aperture device, the aperture device including a portion that is electrically floating relative to a wall of the chamber coupled to the aperture device.

12. The system of claim 11, further comprising means for processing a work piece with an ion beam generated with the ion beam gun, the means for processing including means for conveying the work piece to and from a processing chamber, the processing chamber including an electrode positioned therein.

13. An apparatus, comprising:

an ion gun coupled to a gas source;

a resonator operable to ionize gas received in the chamber from the gas source, the resonator including an RF electrical energy source, a helical coil wound about a portion of the chamber and coupled to the RF electrical energy source and an electrical shield positioned about the helical coil;

a magnetic indexing arrangement including several magnetic coils positioned about the chamber between the gas source and the resonator, a first one and a second one of the magnetic coils having a magnetic field strength greater than a third one of the magnetic coils, the third one of the magnetic coils being positioned between the first one and the second one of the coils; and a focusing arrangement including an aperture device, the aperture device including a portion that is electrically floating relative to a wall coupled to the aperture device.

14. The apparatus of claim 13, further comprising a processing chamber coupled to the chamber to receive an ion beam from the ion gun chamber.

15. The apparatus of claim 14, further comprising an electrode positioned in the processing chamber and electrically isolated therefrom.

16. The apparatus of claim 15, further comprising a first conveyor subsystem coupled to the processing chamber to deliver work pieces to the processing chamber.

17. The apparatus of claim 16, further comprising a second conveyor subsystem coupled to the processing chamber to retrieve work pieces from the processing chamber.

18. The apparatus of claim 15, wherein the processing chamber is electrically grounded and the electrode is negatively biased relative to electrical ground.

19. The apparatus of claim 14, further comprising an inertial electrostatic containment device positioned in the processing chamber.

20. A method, comprising:

providing a gas to an ion beam gun;

ionizing the gas with the ion beam gun, the ion beam gun including an RF resonator, the RF resonator including a helical coil coupled to an RF electrical energy source and an electrical shield positioned about the helical coil;

controlling ionized particles with several magnetic indexing coils;

focusing an ion beam generated with the ion beam gun, the ion beam gun including a focusing arrangement with an aperture device, the aperture device including a portion that is electrically floating relative to a wall coupled to the aperture device; and providing the ion beam to a processing chamber.

* * * * *